United States Patent [19]

Chan et al.

[11] Patent Number: 5,177,024

[45] Date of Patent: Jan. 5, 1993

[54] DETERMINING CEREAL QUALITY

[75] Inventors: Henry W. Chan; Michael R. A. Morgan; Elizabeth N. C. Mills, all of Norwich, England

[73] Assignee: Agricultural & Food Research Counsel, England

[21] Appl. No.: 413,443

[22] Filed: Sep. 27, 1989

[30] Foreign Application Priority Data

Sep. 30, 1988 [GB] United Kingdom ............... 8823027

[51] Int. Cl.⁵ .......................................... G01N 33/536
[52] U.S. Cl. ................................... 436/536; 435/7.1; 435/240.27; 530/387.9; 530/388.5
[58] Field of Search ............... 530/387, 385, 808, 809, 530/375, 387.9, 388.5; 436/536; 435/240.27

[56] References Cited

U.S. PATENT DOCUMENTS 4,826,765  5/1989  Greene et al. ...................... 435/68

OTHER PUBLICATIONS

Sevier et al., Clin. Chem. 27:1797–1806, 1981.

*Primary Examiner*—Esther L. Kepplinger
*Assistant Examiner*—Donna Wortman
*Attorney, Agent, or Firm*—Lerner, David, Littenberg, Krumholz & Mentlik

[57] ABSTRACT

The three amino acid sequence TCP (threonine-crysteineproline) has been found, in wheat glutenin, to correspond to good bread-making qualities in wheat flour. This sequence, and 32 nine amino acid sequences containing it, can be detected by amino acid analysis of the glutenin, by specific monoclonal antibodies or by analysis (e.g. nucleotide sequence analysis or hybridization assays) of the wheat genome.

4 Claims, No Drawings

DETERMINING CEREAL QUALITY

The present invention relates to methods of determining cereal quality, with particular relation to the structure of variants of the cereal protein gluten.

Wheat flour is principally used for making bread or biscuits. Some flours are better suited to bread-making and some to biscuit-making and qualities can vary within each class. Known methods of determining whether a given grain is good for bread-making are very crude and can amount to simply milling some flour and baking a loaf to see what happens.

Payne et al (1981, 1987) have found a strong hereditary correlation between certain gluten subunits, namely glutenin subunits 1, 5 and 10, and bread-making characteristics. The amino acid sequences of some subunits associated with poor bread-making qualities have been determined, but not those associated with good bread-making qualities.

We have now found that the nonapeptide PSVTCPQQV is associated with such properties, and it is thought that the central cysteine residue is particularly important as the formation of disulphide bonds probably influences the quality of the flour. The central TCP entity helps such bonds to be formed.

For the avoidance of doubt, the said nonapeptide may also be represented as Pro-Ser-Val-Thr-Cys-Pro-Gln-Gln-Val. Antibodies can be made to this peptide, portions thereof and variants thereof and used to determine very readily whether, and to what extent, a given sample of wheat grain or flour material has the desired properties.

Accordingly, one aspect of the invention provides an antibody usable to identify, in wheat grain glutenin, a TCP sequence or one of the following sequences:

| | |
|---|---|
| (1) | GSVTCPQQV |
| (2) | GSVSCPQQV |
| (3) | GTVTCPQQV |
| (4) | GSVTCPQQA |
| (5) | GSTTCPQQV |
| (6) | GSVTCPQQT |
| (7) | GSLTCPQQV |
| (8) | GSVTCPQQL |
| (9) | GAVTCPQQV |
| (10) | GSVACPQQV |
| (11) | GSVGCPQQV |
| (12) | GSVNCPQQV |
| (13) | GSVTCPQPV |
| (14) | GSVTCPQQI |
| (15) | GSVTCPQQL |
| (16) | VQQPCTVSG |
| (17) - (32) | | wherein peptides (17) to (32) correspond to (1) to (16) above respectively but have a terminal proline in place of the terminal glycine.

All these sequences have the N-terminal on the left.

The antibody may be used directly, in the sense of recognising one of the said sequences, or indirectly, in the sense of recognising an entity which is characteristic of one of the said sequences. Thus, the wheat glutenin may be modified in ways described below and the antibody in question then recognises the modified structure.

The term "glutenin" originates from Osborne's 1924 classification of vegetable proteins, based on their solubility in different solvents. Glutenin was defined by him as not being soluble in aqueous alcohols. Subsequently these proteins have been solubilised in such solvents by the reduction of disulphide bonds and lowering the pH.

It is now believed that glutenin is made up of polymers comprised of low molecular weight (LMW) and high molecular weight (HMW) subunits. These groups of polypeptides can be defined in terms of their molecular weight, amino acid composition and chromosome locus. However, the latter may not be a very useful characteristic, since some subunits could be coded for by loci not as yet defined, and future varieties of wheat derived by genetic manipulation could have the genes for these proteins at different loci.

(i) HMW Subunits of Glutenin

| Molecular weight: | SDS PAGE | 95–136,000 |
|---|---|---|
| | Sedimentation Equilibrium | 60–70,000 |
| Partial amino acid | Glx (E + Q) | 34–39 |
| Composition (mol %): | Pro (P) | 13–16 |
| | Gly (G) | 14–20 |
| | Phe (F) | 0.3–11 |
| | Cys/2 (C) | 0.4–15 |
| | Met (M) | t–0.4 |
| Gene loci: | Designation | Glu-1 |
| | Locations | 1Al, 1BL, 1DL |

These subunits, in addition to being quite large, are characteristically rich in proline, amide nitrogen and glycine.

(ii) LMW Subunits of Glutenin (also known as HMW gliadin, LMW glutenin, or aggregated gliadin)

| Molecular weight: | SDS PAGE | 36–44,000 |
|---|---|---|
| | Sequencing | 33,000 |
| Partial amino acid | Glx (E + Q) | 38 |
| composition (mol %) | Pro (P) | 15 |
| | Gly (G) | 3.3 |
| | Phe (F) | 4.7 |
| | Cys/2 (C) | 2.7 |
| | Met (M) | 0.6 |
| Gene loci: | basic subunits Gli-1 | |
| | (Location 1AS, 1BS, 1DS) | |
| | acidic subunits Glu-2, | |
| | (Location 1BS, 1DS) | |

Like the HMW subunits, these are rich in prolamine and amide nitrogen. They do, however, contain much more S, particularly as cysteine.

Preferably the TCP sequence is in the glutenin 5 subunit of the glutenin.

Preferably, the antibody is usable to identify a sequence selected from the sequences (1) to (32) given above.

By the phrase "antibodies usable to identify", we mean antibodies which will bind to such sequences or modifications thereof with sufficient selectivity to provide a useful assay. The man skilled in the art will be able to determine readily whether a given antibody satisfies this criterion. The affinity constants (K) of the antibodies preferably range from $10^4$ to $10^9$ $M^{-1}$. Low affinity antibodies (e.g. $K = 1 \times 10^5 M^{-1}$) tend to be of the IgM isotype, and their low affinity is compensated for by multivalency since they possess ten antibody binding sites. If all the sites are available, for binding, such an antibody would have an effective, or functional, affinity (or avidity) of $10 \times K$. Higher affinity antibodies ($K = 1 \times 10^6 M^{-1}$ or greater, preferably $1 \times 10^7 M^{-1}$ or greater) are of more practical usefulness in devising an assay, but for certain applications low affinity antibodies have some advantages.

Preferably, the antibody is a monoclonal antibody, although polyclonal sera of restricted specificity can be prepared by presenting the peptide sequence suitably in an antigenic formulation administered to a mammal, and/or by screening a pool of antibodies with a suitable peptide.

A second aspect of the invention provides a process for the preparation of an antibody as defined above by (a) screening a pool of antibodies for those having selective affinity for a peptide sequence defined above, or (b) raising monoclonal antibodies as defined above.

In process (a), the pool of antibodies may, for example, be prepared by immunising a vertebrate with wheat gluten or with one or more fragments or modifications thereof, and obtaining serum from the vertebrate.

In process (b), a vertebrate may be immunised with wheat gluten or with one or more fragments or modifications thereof and one or more suitable cells, for example spleen cells, may be taken from the vertebrate and fused with a substantially immortal cell line according to the general principles of Milstein and Köhler to prepare a hybridoma from which monoclonal antibodies may be isolated. In both processes (a) and (b), the "fragment" may be a peptide (1) to (32) as above, preferably GSVTCPQQV, coupled to a suitable immunogenic carrier, for example BSA. The screening for antibodies may involve an immobilised peptide (1) to (32) or another peptide, for example GSVTCPNQV or GSVTCPGQV, as explained below.

A third aspect of the invention provides a peptide selected from the following:

| (A) TCP |
| --- |
| (1) GSVTCPQQV |
| (2) GSVSCPQQV |
| (3) GTVTCPQQV |
| (4) GSVTCPQQA |
| (5) GSTTCPQQV |
| (6) GSVTCPQQT |
| (7) GSLTCPQQV |
| (8) GSVTCPQQL |
| (9) GAVTCPQQV |
| (10) GSVACPQQV |
| (11) GSVGCPQQV |
| (12) GSVNCPQQV |
| (13) GSVTCPQPV |
| (14) GSVTCPQQI |
| (15) GSVTCPQQL |
| (16) VQQPCTVSG |
| and (17) to (32) as above | and such conservatively modified variants thereof as may be used to make or select antibodies usable to identify one of the said sequences, and especially PSVTCPQQV, in wheat glutenin. Two such series of conservatively modified variants have an asparagine or glycine, respectively, in place of the N-terminal glutamine, examples being GSVTCPNQV and GSVTCPGQV. These are particularly useful in selecting useful monoclonal antibodies raised using PSVTCPQQV as the immunogen.

These modifications help to ensure that MAbs specific for the cysteine residue are selected, rather than MAbs specific only for the type 1-3 β-turn which is created by the TCP entity. As with selection using any of sequences (1) to (32), the modified peptide used for selection will usually be immobilised, for example on bovine thyroglobulin.

Shorter sequences may be used to raise and/or select the desired antibodies, for example those lacking up to three N-terminal and/or up to three C-terminal residues. Whether a given candidate peptide can be used to produce a sufficiently specific antibody may readily be determined in a non-inventive fashion by the man skilled in the art.

Preferably, in any such conservative modifications, the N-terminal glycine is retained or replaced by a proline and preferably the CPQ sequence is retained.

It may be advantageous for the antibody to be raised with, and/or selected with, a peptide which is modified, for example by acylation of the cysteine residue. This may yield peptides which are more antigenic. It will then usually be necessary to modify the wheat glutenin in a corresponding way before performing the assay. The thiol group of the cysteine residue may be modified with an acylating agent (such as succinic anhydride, ethylthiotrifluoroacetate or acetylchloride), a carbonyl compound (such as acetaldehyde), an alkylating or arylating agent (such as iodoacetic acid, iodoacetamide, 2,4,6,-trinitrobenzene sulphonic acid, 4-vinylpyridine, N-ethylmaleimide, or fluoro-2,4,-dinitrobenzene), an organomercurial (such as p-mercuribenzoic acid), an arsenical compound (such as tetravalent arsenic) or a disulphide (such as 5,5-dithio-bis-(2-nitrobenzoic acid). The methods of use are conventional and are described in Torchinski, Y M, Sulphur in Proteins, Pergamon Press, Oxford (Metzler, D. Tran. Ed.) 1981. The terms "conservatively modified variant" or "modification" are used to include such modified peptides.

A fourth aspect of the invention provides a method of analysing wheat glutenin comprising determining whether the glutenin contains a cysteine residue at position 97 or, more specifically, a sequence selected from the following:

| (A) TCP |
| --- |
| (1) GSVTCPQQV |
| (2) GSVSCPQQV |
| (3) GTVTCPQQV |
| (4) GSVTCPQQA |
| (5) GSTTCPQQV |
| (6) GSVTCPQQT |
| (7) GSLTCPQQV |
| (8) GSVTCPQQL |
| (9) GAVTCPQQV |
| (10) GSVACPQQV |
| (11) GSVGCPQQV |
| (12) GSVNCPQQV |
| (13) GSVTCPQPV |
| (14) GSVTCPQQI |
| (15) GSVTCPQQL |
| (16) VQQPCTVSG |
| or (17) to (32) as above. |

Preferably, the analysis is such as to determine whether the glutenin comprises the sequence PSVTCPQQV.

The glutenin may be extracted from the wheat grain by known techniques, for example those described in Miflin et al, 1983. The total glutenin fraction may be present or, more preferably, only the high molecular weight fraction thereof.

Such analysis may comprise exposing the wheat material to an antibody which indicates, directly or indirectly, the presence of one or more of the said sequences. The analysis may be performed by any suitable known or future analytical technique involving the said antibody, for example an enzyme-linked immunosorbent assay (ELISA), radio-immunoassay (RIA), competition binding assays and so on.

If the antibody recognises a modified peptide, then it will usually be necessary to modify the wheat sample before applying the assay. Typically, the prolamins are extracted from a sample of wheat by grinding in a buffer consisting of 0.1M phosphate buffer, pH 7.0, 6M urea, 1% (v/v) mercaptoethanol. If N-ethylmaleimide is the modifying agent, then, to 1 ml of extract, 35 mg of N-ethylmaleimide would be added and the solution incubated at room temperature for 20 mins. If iodoacetamide is the modifying agent, then the pH of the extract is adjusted to 9.0 with 5M NaOH, and 1 ml is placed in a light-proofed container. Next, 100 mg of iodoacetamide is added, and allowed to react for 30 mins at room temperature. The modification reactions in either case are then terminated by the addition of 0.1 ml of mercaptoethanol. Samples are then diluted into a suitable buffer, such as phosphate buffered saline, prior to use. Other methods of using these and other modifying agents will be known to those skilled in the art of protein chemistry.

Alternatively, the genome of the wheat may be analysed for the presence of nucleotide sequences encoding any of the said peptide sequences. Such analysis may take the form of exposing the DNA of the wheat to a labelled probe and detecting hybridisation in a known fashion. Direct nucleotide sequencing, using methods such as those of Maxam and Gilbert or Sanger, is available to the man skilled in the art for analysis of genomes.

Suitable oligonucleotide probes useful for hybridising to wheat DNA or RNA form a further aspect of the invention.

The nonapeptides listed above correspond to positions 93 to 101 of high molecular weight (HMW) glutenin subunit 5. In the naturally-occurring protein, residue 93 is a proline. In peptides (1) to (16) above, this is changed to a glycine so that carbodiimide linking to the carrier protein may be used; this does not significantly affect the binding properties of the antibody prepared thereto. Different coupling agents may allow a terminal proline to be used, as in peptides (17) to (32). DNA analyses or amino acid analyses would clearly be directed to peptide (17) and variants thereof in preference to peptide (1) and variants thereof.

Such analytical techniques will be of benefit to millers wishing to control the quality of the flour which they buy, and also to cereal breeders who can readily determine the bread-making quality of a new strain of cereal and thereby accelerate their cross-breeding programmes.

In this way, improved strains of wheat can be created which combine bread-making properties with desirable properties associated with non-bread-making kinds of wheat.

The following Examples illustrate preferred aspects of the invention in a non-limiting manner.

EXAMPLE 1: PRODUCTION OF ANTIBODIES

1.1 Production of Peptide Conjugates

Synthetic peptides were made using the known tertiarybutyloxycarbonyl method. They were then covalently linked to a carrier protein, namely bovine serum albumin (BSA) or thyroglobulin at 10 mg peptide to 8 mg carrier, using 100 mg of 1-ethyl-3-(3-dimethylaminopropyl) carbodiimide in 50 mM phosphate buffer, pH 6.5 and purified by column chromatography.

1.2. Production of monoclonal antibodies

Balb/c mice were immunised with total gluten preparations or peptide conjugates (50 μg) emulsified in Freund's complete adjuvant:saline (7:3, v:v), administered by intraperitoneal injection. Subsequent booster injections were administered at intervals of at least one month, replacing complete with incomplete Freund's adjuvant. The response of the animals was monitored by taking samples of blood from the tail and assaying for serum antibody activity using the enzyme-linked immunosorbent assay, ELISA, described below. Once an adequate antibody response had been attained, an animal was given a final booster injection 4 days prior to performing a fusion.

Spleen cells were prepared from the mouse and were fused with the mouse myeloma line X63 Ag8 653 (Flow Laboratories) in a ratio of 5:1 using polyethylene glycol, following the method of Galfré and Milstein. The fused cells were distributed between four 96-well microtitration plates in Optimem (Flow Laboratories) supplemented with 4% foetal calf serum (FCS), hypoxanthine, aminopterin and thymidine. Fourteen days after the fusion, culture supernatants were screened by ELISA for antibody activity against total gliadins. Cells in antibody-positive wells were then expanded into 24-well plates, and cloned by limiting dilution using Optimem supplemented with 4% (v/v) FCS, hypoxanthine and thymidine, together with rat erythrocytes as feeder cells. Cloned cell lines were grown up in Optimem supplemented with FCS at levels ranging from 0.2-4% (v/v), depending upon the cell-line. Monoclonal antibodies were concentrated by precipitation with 50% ammonium sulphate at 4° C. The precipitate was pelleted by centrifugation at 10,000 g at 4° C. for 30 mins, and then resuspended in phosphate-buffered saline (PBS, 0.1M phosphate-buffered saline, pH 7.4). After dialysing against several changes of PBS, the concentrated antibodies were stored at 4° C. in the presence of 0.05% (w/v) thiomersal. (Galfré & Milstein, 1981).

1.3 Characterisation of Antibodies

Polystyrene microtitration plates (Nunc Immunoplate 1) were coated by filling the wells with 0.3 ml of 0.05M carbonate/bicarbonate buffer, pH 9.6, containing the relevant peptide-conjugate at 1 μg/ml (for screening purposes). After overnight incubation at 4° C., plates were washed three times with water using a Titertek microplate washer, dried by shaking out excess water and stored at −20° C. until required. Prior to use, plates were washed three times in PBS-Tween. Screening of tissue culture medium for antibody activity was performed by transferring 0.15 ml of medium from culture plates to assay plates and incubating overnight at 4° C. Plates were then washed five times with PBS-Tween before adding 0.2 ml/well of anti-mouse IgG-horseradish peroxidase (Sigma Chemical Co) diluted 1:1000 (v:v) in PBS-Tween and incubating for 3 hr at 37° C. Unbound enzyme-labelled antibody was removed by washing five times with PBS-Tween, and 0.2 ml/well of substrate (Cambridge Life Sciences) added. After a 30 min incubation at 37° C. the reaction was stopped by the addition of 50 μl/well of 2M $H_2SO_4$ and the optical density measured at 450 nm using a Titertek MCC automatic plate reader.

EXAMPLE 2: ANALYSIS OF WHEAT GRAIN BY ELISA

The initial steps of the assay involve the solubilisation of the grain protein by grinding wheat in a suitable buffer, for example one comprising 6M urea, or 25% (v/v) propanol, 1% (v/v) acetic acid and 1% (v/v) mercaptoethanol, and subsequent dilution of the extract in a suitable buffer such as phosphate-buffered saline.

2.1 Microtitration Plate Two-Site ELISA

This type of immunoassay employs a broader specificity monoclonal antibody as a capture antibody, adsorbed to the polystyrene microtitration plates. Extracts of the unknown samples or standards of known baking quality are then incubated on these plates, the capture antibody binding the gluten proteins present in the extracts. After washing away unbound material, a monoclonal antibody specific for the nonapeptide is added. This second antibody is labelled with a tag to allow generation of a quantifiable end-point. A variety of tags are available including colloidal gold, fluorescene tags such as FITC, chemiluminescence tags and enzyme labels which can be quantified by the addition of substrate. A suitable label is horse-radish peroxidase, and this can be quantified using the substrate described above. The coloured product generated is determined spectrophotometrically and the baking quality of the unknowns determined by comparison with the standards of known baking quality.

2.2 Dip-stick Assay

A dip-stick type immunoassay employs a probe coated with a general monoclonal antibody of broad specificity, which can be dipped into the diluted extract, allowing the solubilised protein to bind. After washing, the dip-stick is then incubated with the peptide-specific monoclonal antibody coupled to an enzyme such as horse-radish peroxidase. After further washing, the amount of enzyme label (and hence nonapeptide present in the extract) is assessed by placing in the appropriate substrate solution, and monitoring the amount of coloured product produced. A coded card may be provided to relate the amount of colour produced to baking quality.

EXAMPLE 3: GENE PROBE ASSAY

This approach has the limitation, compared to that based on antibody technology, of not being able to assess the level of expression of genes containing the sequence. In other words, the gene may be expressed only poorly or, if in for example a pseudogene, not at all. The quality of the wheat will be dictated more by the amount of this sequence present as protein than by a straight presence/absence relationship.

For a gene-probe assay, DNA is first isolated from the grain to be analysed by known techniques. This DNA is then hybridised with a synthetic oligonucleotide (for example 27 mer) probe corresponding to at least part of the DNA sequence coding for GSVTCPQQV. The probe is labelled to enable detection, using either a radiolabel such as 32P or some type of chemical tag such as biotin which could be visualised colorimetrically. The actual hybridisation step may take several forms, two of which are given below:

3.1 After isolating the wheat DNA, a restriction enzyme digest is performed, optimised to give DNA fragments 1-3 kb, a size optimal for detecting single point mutations. After separating the digest by agarose gel electro-phoresis, the gel is hybridised with the labelled probe, and the binding assessed in a manner appropriate to the type of label employed.

3.2 Isolated wheat DNA is immobilised to a membrane, such as nitrocellulose, and then probed using the labelled 27 mer. Binding is assessed as for the restriction enzyme digest. The use of a filter system, set out on a microtitration plate format, enables a quantitative assessment to be carried out and lends itself far more to routine screening of large numbers of samples.

EXAMPLE 4: DOT-BLOT ASSAY

This assay is based on binding of the gluten proteins to be analysed onto a nitrocellulose membrane (or some equivalent support such as "Zeta bind") which can then be probed using an antibody specific for gluten quality factors. Samples are extracted in solvents, such as 6M urea, or 25% (v/v) propanol, 1% (v/v) acetic acid, 1% (v/v) mercaptoethanol and diluted appropriately in a buffer such as phosphate-buffered saline (PBS). Aliquots (such as 1–10 µl) of diluted sample and standards of known baking quality are applied to nitrocellulose paper. After drying, this dot-blot is then incubated in a blocking solution such as 3% (w/v) bovine serum albumin in PBS, for 1 hour, at 37° C. with shaking. After rinsing the dot-blot 3 times in phosphate-buffered saline containing 0.05% v/v Tween 20 (PBS Tween), the dot-blot is incubated with the antibody specific for gluten quality factors for 1 hour at 37° C., with shaking. ("Tween" is a Registered Trade Mark). After washing a further 3x in PBS Tween the binding of this specific antibody is then quantitated in a variety of ways:

a) the specific antibody is radiolabelled by iodination or, for a monoclonal antibody, labelled with $^3$H or $^{14}$C by growing the hybridomas in medium containing radiolabelled amino acids. The binding of such labelled antibodies to the dot-blot is then quantitated by counting the nitrocellulose paper in a gamma-counter ($^{125}$I) or using liquid scintillation counting ($^3$H or $^{14}$C).

b) the specific antibody is labelled with an enzyme such as alkaline phosphatase or horse-radish peroxidase. The binding of the enzyme-labelled antibody is then quantitated by incubating the dot-blot with the appropriate substrate. Thus, when employing alkaline phosphatase, the dot-blot is incubated with 200 mM Tris HCl pH 8.0, 2 mM $MgCl_2$, 3 mg/ml Fast red TR and 0.2 mg/ml naphthol ASTR phosphate. Samples of gluten to which the antibody bound are denoted by the appearance of pink spots on the dot-blot. After a 15 min incubation with substrate the reaction is stopped by rinsing the dot-blot in water. When employing horse-radish peroxidase as the enzyme label, the dot-blot is incubated with a supersaturated solution of chloronaphthol in PBS containing 0.1% $H_2O_2$, in the dark for 15 mins. Antibody binding to the dot-blot is denoted by the presence of purple spots. The reaction is terminated by rinsing the dot-blot in water.

c) the specific antibody is labelled with biotin, and the dot-blot incubated with avidin labelled with horse-radish peroxidase or alkaline phosphatase diluted 1:1000 (v:v) in PBS Tween, for 1 hr at 37° C. with shaking After rinsing 3× in PBS Tween, the blot is developed as in b) above.

d) the dot-blot is incubated with anti-mouse IgG or IgM (depending on the isotype of the specific antibody), protein A or protein G labelled with alkaline phosphatase or horse-radish peroxidase diluted 1:1000 (v:v) in PBS Tween for 1 hr at 37° C., with shaking. After rinsing 3× in PBS Tween the blot is developed as in b) above.

EXAMPLE 5: LATEX AGGLUTINATION ASSAYS

The antibody specific for gluten quality components is covalently coupled to latex particles (up to 0.8 μm in diameter). Samples are extracted as described for the dot-blot assay, and then diluted appropriately in phosphate-buffered saline, 0.05% (v/v) Tween 20 and 1% (w/v) bovine serum albumin. Replicates of unknown samples and standards are added to a microtitration plate (50 μl/well) together with 50 μl/well of antibody-coated latex particles diluted appropriately in phosphate-buffered saline, 0.05% (v/v) Tween 20. After shaking the plate gently for a few seconds, the plate is incubated for 30 min at 37° C. A positive reaction is denoted by an even coating of latex particles across the surface of a well, a negative reaction indicated by the latex particles settling into a tight button or ring at the bottom of a well.

In addition to such a visual end-point, the degree of agglutination may be assessed by counting the particles that remain in solution after the agglutination has taken place, using an optical system. The degree of agglutination may also be assessed by performing the assay in a centrifugal analyser of the type routinely used in clinical chemistry laboratories. In this case diluted sample and antibody coated latex particles are loaded into the analyser, mixed by centrifugation and the light scattering caused by the agglutination monitored by the optical system of the analyser at 600 nm.

EXAMPLE 6: CELL AGGLUTINATION ASSAYS

The antibody specific for gluten quality components is covalently coupled to sheep or human erythrocytes. Samples are extracted as described for the dot-blot assay, and then diluted appropriately in phosphate-buffered saline 1% (w/v) bovine serum albumin. Samples of known baking quality are treated similarly. Replicates of unknown samples and standard are added to a microtitration plate (50 μl/well), together with 50 μl/well of a 1% (v/v) suspension of the coupled erythrocytes. After shaking the plate for a few seconds, the erythrocytes are allowed to settle for about 1 hr. A positive reaction is denoted by an even coating of cells across the surface of a well, whereas a negative reaction is indicated by the cells settling into a tight button, or ring at the bottom of a well.

Such an assay may be performed equally well using tubes or microscope slides.

EXAMPLE 7: MAGNETIC PARTICLE IMMUNOASSAY

A broad-specificity monoclonal antibody is coupled to magnetic particles. 0.3 ml of stock antibody-magnetic particle solution in PBS Tween is added to each tube. Samples and standards of known baking quality are extracted as described for the dot-blot assay, and diluted appropriately in PBS Tween. Each sample/standard is assayed in duplicate, 0.5 ml of diluted extract being added to the magnetic particles. After incubating for 2 hrs at 37° C., the magnetic particles are brought down using a magnetic separator, and washed in 1 ml/tube of PBS Tween. This washing procedure is repeated three times before adding 0.5 ml/tube of a monoclonal antibody specific for the nonapeptide, labelled with either alkaline phosphatase or horseradish peroxidase. After incubating for a further 2 hr at 37° C., and a further 3 washes in PBS Tween, the substrate (1.0 ml/tube) is added and incubated for 30 min. at 37° C. For alkaline phosphatase conjugates 1 mg/ml phosphatase substrate (Sigma Chemical Co.) dissolved in 0.05M sodium carbonate-bicarbonate buffer containing 2 mM $MgCl_2$ was used whilst, for horseradish peroxidase, a tetramethylbenzidine based substrate from Cambridge Life Sciences (UK) was used.

When the nonapeptide specific antibody is not enzyme labelled, this assay is performed by adding an extra incubation. After adding the specific antibody and incubating, the magnetic particles are washed 3× in PBS Tween, and then incubated for 2 hrs at 37° C. with 0.5 ml/tube of anti-mouse IgG or IgM (depending on the isotype of the specific antibody) diluted 1:1000 (v:v) in PBS Tween. The assay then proceeds as above.

The amount of coloured produce produced in this assay can be determined spectrophotometrically. The baking quality of unknown samples can then be assessed by comparing the optical densities obtained with those for the standards of known baking performance.

EXAMPLE 8: CARD-TYPE ASSAYS

For this type of assay an antibody of broad specificity for gluten is immobilised to a porous nylon membrane. This is then supported by a porous polyethylene disc which is mounted on an absorbant pad composed of cellulose acetate. The whole pad-like device is then incorporated into a card-format of the size of a credit-card. Samples are extracted as for the dot-blot assay, and diluted appropriately in phosphate-buffered saline, 0.05% (v/v) Tween 20 (PBS Tween). Diluted sample (0.2 ml) is applied to the membrane and incubated at room temperature for 1 min, followed by 0.5 ml of PBS Tween. The anti-nonapeptide antibody conjugated to alkaline phosphatase is then added (0.1 ml) and after a further 1 min incubation at room temperature, 0.5 ml of PBS Tween is again added. Once the membrane has drained, 0.15 ml of substrate as for the dot-blot development using alkaline phosphatase as the label.

The assay is then terminated by adding a further 0.5 ml of PBS Tween. A positive assay is denoted by the presence of a pink colour on the pad. The baking quality is then assessed by comparison with standard of known quality run in parallel, or by comparison with a shade guide relating the intensity of the pink colour to baking quality.

EXAMPLE 9: EVANESCENT WAVE IMMUNOASSAY

In this type of assay, the anti-nonapeptide antibody is coated onto an evanescent wave guide made of a quartz fibre or slide. This coated wave guide is then placed into the sample extract (prepared as described for the dot-blot) diluted in phosphate buffered saline 0.05% (v/v) Tween, and incubated for 10 min at room temperature. When the gluten proteins bind, there is a change in the transmitted light intensity. The system is calibrated using a series of standard samples of known baking quality.

EXAMPLE 10: RADIOIMMUNOASSAY

Samples are extracted as described for the dot-blot assay, and diluted appropriately in phosphate buffered saline (PBS). A 0.2 ml aliquot of each sample, in duplicate, is mixed with 0.2 ml of $^{125}I$- or $^{3}H$-labelled nonapeptide (approximately 50 Ci/mmol) in PBS containing 0.1% (w/v) bovine serum albumin (BSA). This is then incubated with 0.4 ml of anti-nonapeptide antibody diluted appropriately in PBS, 0.1% BSA overnight at 4° C. Dextran coated charcoal (0.3% (v/v) in PBS containing 0.05% (w/v) dextran, 0.1% BSA) is then added (1 ml/tube) and, after incubating at 0° C. for 30 min, the charcoal is removed by centrifuging 10 min. at 2,000 xg. Supernatants are then decanted into scintillation vials with 5 mls of scintillation cocktail (for the $^3$H labelled peptide only) prior to counting, or counted in a gamma-counter ($^{125}$I-labelled peptide). The greater the amount of peptide present in the sample, the lower the counts will be. Baking quality of samples is assessed by reference standard samples of known baking quality included in each bath of analysis. Baking quality is also analysed by quantitating the amount of peptide present. This is achieved by generating a standard curve for the radioimmunoassay by substituting the sample extracts with free peptide standards 10–10,000 pg/tube.

References

Galfré, G and Milstein, C. In: Methods in Enzymology 73, p.3–46 (1981).

Payne, P. I., Corfield, K. G., Holt, L. M. and Blackman, J. A. J. Science Food Agriculture 32 51–60 (1981).

Payne, P. I., Nightingale, M. A., Krattiger, A. F., and Holt, L. M. J. Science Food Agriculture 40 51–65 (1987).

Miflin, B. J., Field, J. M. and Shewry, P. R. In: Seed Proteins (ed. J. Dausscent, J. Mosse, and J. Vaughan) Academic Press 1983 pp 255–319).

We claim:

1. A method of determining wheat characteristics comprising the steps of: contacting wheat glutenin with an antibody that specifically binds an amino acid sequence selected from the group consisting of GSVTCPQQV, GSVSCPQQV, GTVTCPQQV, GSVTCPQQA, GSTTCPQQV, GSVTCPQQT, GLSTCPQQV, GSVTCPQQL, GAVTCPQQV, GSVACPQQV, GSVGCPQQV, GSVNCPQQV, GSVTCPQPV, GSVTCPQQI, GSVTCPQQL, VQQPCTVSG, substitutions of the foregoing sequences wherein a terminal glycine is substituted with proline, TCP, and PSVTCPQQV; and detecting the formation of an immune complex between said antibody and the wheat glutenin.

2. A composition consisting essentially of an isolated and purified antibody that specifically binds to a sequence selected from the group consisting of: GSVTCPQQV, GSVSCPQQV, GTVTCPQQV, GSVTCPQQA, GSTTCPQQV, GSVTCPQQT, GLSTCPQQV, GSVTCPQQL, GAVTCPQQV, GASVACPQQV, GSVGCPQQV, GSVNCPQQV, GSVTCPQPV, GSVTCPQQI, GSVTCPQQL, VQQPCTVSG; substitutions of the foregoing sequences wherein a terminal glycine is substituted with proline; TCP; and PSVTCPQQV.

3. The composition of claim 2, wherein said antibody is a monoclonal antibody.

4. A hybridoma that secretes said monoclonal antibody of claim 3.

* * * * *

UNITED STATES PATENT AND TRADEMARK OFFICE
CERTIFICATE OF CORRECTION

PATENT NO. : 5,177,024
DATED : January 5, 1993
INVENTOR(S) : Chan et al

It is certified that error appears in the above-indentified patent and that said Letters Patent is hereby corrected as shown below:

In the Abstract, line 2, "(threonine-crysteineproline)" should read --(threonine-cysteine-proline).
Column 11, line 14, "($1^{25}$I-labelled" should read --($^{125}$I-labelled--

Signed and Sealed this

Twenty-sixth Day of October, 1993

Attest:

BRUCE LEHMAN

Attesting Officer

Commissioner of Patents and Trademarks